US012599398B2

(12) United States Patent　　　　(10) Patent No.:　US 12,599,398 B2

Thatipelli　　　　　　　　　　　　　(45) Date of Patent:　Apr. 14, 2026

---

(54) DEVICE AND METHOD FOR CENTERING AND CROSSING A VASCULAR OCCLUSION

(71) Applicant: AngioSafe, Inc., San Jose, CA (US)

(72) Inventor: Mallik Thatipelli, Bakersfield, CA (US)

(73) Assignee: AngioSafe, Inc., San Jose, CA (US)

( * ) Notice: Subject to any disclaimer, the term of this patent is extended or adjusted under 35 U.S.C. 154(b) by 321 days.

(21) Appl. No.: 17/468,279

(22) Filed: Sep. 7, 2021

(65) Prior Publication Data

US 2021/0401455 A1　　Dec. 30, 2021

Related U.S. Application Data

(62) Division of application No. 15/905,491, filed on Feb. 26, 2018, now Pat. No. 11,123,098.

(60) Provisional application No. 62/465,108, filed on Feb. 28, 2017.

(51) Int. Cl.
　　*A61B 17/3207*　　(2006.01)
　　*A61B 17/22*　　　(2006.01)
　　*A61B 90/00*　　　(2016.01)

(52) U.S. Cl.
　　CPC .............. *A61B 17/320758* (2013.01); *A61B 17/320725* (2013.01); *A61B 2017/22039* (2013.01); *A61B 2017/22068* (2013.01); *A61B 2017/22094* (2013.01); *A61B 2017/320766* (2013.01); *A61B 2090/08021* (2016.02)

(58) Field of Classification Search
　　CPC ........ A61B 17/320758; A61B 17/3207; A61B 17/320725; A61B 2017/22094
　　See application file for complete search history.

(56) References Cited

U.S. PATENT DOCUMENTS

| | | | |
|---|---|---|---|
| 888,801 | A | 5/1908 | Hammer |
| 4,781,186 | A | 11/1988 | Simpson et al. |
| 4,936,845 | A | 6/1990 | Stevens |
| 5,364,395 | A | 11/1994 | West, Jr. |

(Continued)

FOREIGN PATENT DOCUMENTS

| | | |
|---|---|---|
| CN | 205163174 U | 4/2016 |
| JP | 2001509685 A | 7/2001 |

(Continued)

OTHER PUBLICATIONS

Extended European Search Report dated Nov. 3, 2020 for EP18761615.

(Continued)

*Primary Examiner* — Katherine H Schwiker
*Assistant Examiner* — Zehra Jaffri
(74) *Attorney, Agent, or Firm* — Wilson Sonsini Goodrich & Rosati

(57)　　　　ABSTRACT

A catheter for centrally crossing an occluded blood vessel includes a catheter body having a distal end, a proximal end, and a central passage. A rotatable drive shaft extending through the central passage and has a distal end, a proximal end, and a central lumen. A cutting tip is mounted on the distal end of the rotatable drive shaft and configured to cut through occlusive material when rotated. A plurality of spiral or other flat springs is disposed circumferentially about a distal portion of the catheter body to maintain centering of the catheter and form a passage as the catheter is advanced through a chronic total occlusion.

19 Claims, 8 Drawing Sheets

(56)                References Cited

U.S. PATENT DOCUMENTS

| | | | |
|---|---|---|---|
| 5,843,103 | A | 12/1998 | Wulfman |
| 6,126,667 | A | 10/2000 | Barry et al. |
| 6,156,047 | A | 12/2000 | Spaulding |
| 6,579,298 | B1 | 6/2003 | Bruneau et al. |
| 6,599,304 | B1 | 7/2003 | Selmon et al. |
| 7,306,617 | B2 | 12/2007 | Majercak |
| 7,708,749 | B2 | 5/2010 | Simpson et al. |
| 7,763,012 | B2 | 7/2010 | Petrick et al. |
| 8,021,330 | B2 | 9/2011 | Mcandrew et al. |
| 8,052,704 | B2 | 11/2011 | Olson |
| 8,062,316 | B2 | 11/2011 | Patel et al. |
| 8,192,452 | B2 | 6/2012 | Moberg |
| 8,236,016 | B2 | 8/2012 | To et al. |
| 8,241,315 | B2 | 8/2012 | Jenson et al. |
| 8,361,094 | B2 | 1/2013 | To et al. |
| 8,556,926 | B2 | 10/2013 | Duerig et al. |
| 8,888,801 | B2 | 11/2014 | To et al. |
| 9,060,806 | B2 | 6/2015 | Thatipelli |
| 11,123,098 | B2 | 9/2021 | Thatipelli |
| 2001/0031981 | A1* | 10/2001 | Evans ................... A61B 17/221 |
| | | | 606/200 |
| 2002/0128677 | A1 | 9/2002 | Duerig et al. |
| 2003/0163126 | A1 | 8/2003 | West, Jr. |
| 2003/0236564 | A1 | 12/2003 | Majercak |
| 2005/0004585 | A1 | 1/2005 | Hall et al. |
| 2005/0038462 | A1 | 2/2005 | Lubock et al. |
| 2005/0090845 | A1 | 4/2005 | Boyd |
| 2005/0171572 | A1 | 8/2005 | Martinez |
| 2005/0171592 | A1 | 8/2005 | Majercak |
| 2005/0216044 | A1 | 9/2005 | Hong |
| 2005/0222663 | A1 | 10/2005 | Simpson et al. |
| 2006/0074442 | A1 | 4/2006 | Noriega et al. |
| 2006/0100662 | A1 | 5/2006 | Daniel et al. |
| 2007/0083193 | A1 | 4/2007 | Werneth et al. |
| 2007/0208361 | A1 | 9/2007 | Okushi et al. |
| 2008/0051812 | A1 | 2/2008 | Schmitz et al. |
| 2008/0065125 | A1 | 3/2008 | Olson |
| 2008/0188811 | A1* | 8/2008 | Kim ............... A61B 17/320725 |
| | | | 604/93.01 |
| 2008/0281323 | A1 | 11/2008 | Burbank et al. |
| 2009/0270714 | A1 | 10/2009 | Duffy et al. |
| 2010/0082051 | A1 | 4/2010 | Thorpe et al. |
| 2010/0168557 | A1 | 7/2010 | Deno et al. |
| 2010/0318178 | A1 | 12/2010 | Rapaport et al. |
| 2011/0022045 | A1 | 1/2011 | Cao et al. |
| 2011/0087254 | A1* | 4/2011 | Welty ............. A61B 17/320758 |
| | | | 606/159 |
| 2011/0118660 | A1 | 5/2011 | Torrance et al. |
| 2011/0152920 | A1 | 6/2011 | Eckhouse et al. |
| 2012/0239064 | A1* | 9/2012 | Cartier ........... A61B 17/320758 |
| | | | 606/159 |
| 2012/0239073 | A1 | 9/2012 | Hubregtse et al. |
| 2012/0253186 | A1 | 10/2012 | Simpson et al. |
| 2012/0283565 | A1 | 11/2012 | Richter |
| 2014/0277004 | A1 | 9/2014 | Thatipelli |
| 2014/0277009 | A1 | 9/2014 | Thatipelli |
| 2014/0277015 | A1 | 9/2014 | Stinis |
| 2015/0150587 | A1 | 6/2015 | Smith et al. |
| 2016/0374715 | A1* | 12/2016 | McPeak ......... A61B 17/320758 |
| | | | 606/159 |
| 2018/0242999 | A1 | 8/2018 | Thatipelli |
| 2019/0239907 | A1 | 8/2019 | Brady et al. |
| 2020/0155194 | A1 | 5/2020 | Schneider et al. |

FOREIGN PATENT DOCUMENTS

| | | |
|---|---|---|
| JP | 2008504940 A | 2/2008 |
| JP | 2011045719 A | 3/2011 |
| JP | 2016510680 A | 4/2016 |
| WO | WO-2014158866 A1 | 10/2014 |
| WO | WO-2018160741 A1 | 9/2018 |

OTHER PUBLICATIONS

Office action dated Apr. 6, 2020 for U.S. Appl. No. 15/905,491.

PCT/US2018/020287 International Search Report dated May 4, 2018.

U.S. Appl. No. 15/905,491 Notice of Allowance dated May 26, 2021.

EP23197938.6 Extended European Search Report dated Mar. 11, 2024.

Co-pending U.S. Appl. No. 18/951,495, inventor Thatipelli; Mallik, filed on Nov. 18, 2024.

Roy, Trisha, et al. Puncturing Plaques: Relating MRI Characteristics of Peripheral Artery Lesions to Guidewire Puncture Forces. Journal of Endovascular Therapy 1-12 (2016).

U.S. Appl. No. 18/951,495 Office Action dated Feb. 10, 2025.

Astato® XS 20 0.014 inch, Peripheral Guide Wires. Asahi Inteccusa Medical; [retrieved on Sep. 1, 2025]. Available at URL: https://asahi-inteccusa-medical.com/product/astato-xs-20/ pp. 1-2.

Astato® XS 40 0.014 inch, Peripheral Guide Wires. Asahi Inteccusa Medical; [retrieved on Sep. 1, 2025]. Available at URL: https://asahi-inteccusa-medical.com/product/astato-xs-40/ pp. 1-2.

U.S. Appl. No. 18/951,495 Office Action dated Jun. 3, 2025.

U.S. Appl. No. 18/951,495 Office Action dated Nov. 5, 2025.

* cited by examiner

DEVICE AND METHOD FOR CENTERING AND CROSSING A VASCULAR OCCLUSION

CROSS-REFERENCE TO RELATED APPLICATION

The present application is a divisional of U.S. patent application Ser. No. 15/905,491, filed Feb. 26, 2018, which claims the benefit of provisional application No. 62/465,108, filed on Feb. 28, 2017, the full disclosure of which is incorporated herein by reference.

BACKGROUND OF THE INVENTION

Chronic total occlusions (CTO) are vascular lesions that block most or all blood flow through a blood vessel. CTO's can occur any in most blood vessels, including coronary arteries, carotid arteries, iliac arteries and veins, femoral arteries and veins, and popliteal arteries and veins. Usually CTO lesions will develop over the course several months to years. Due to this chronic pathology, there usually will be an adequate amount time to for development of collateral vessels to supply blood to tissue. These collateral vessels, however, often fail provide enough blood flow to keep organs alive and support their proper functioning.

Over the years, many catheters have been proposed for the treatment of CTO's. Of particular interest herein, U.S. Pat. No. 9,060,806, invented by the inventor herein describes a catheter. The catheter has a motor-driven or other rotatable distal cutter and a plurality of laterally deployable centering elements. While quite effective, the centering elements on this design were not always able to maintain centering when crossing certain hard lesions and the motor-driven or other rotatable distal cutter could be difficult to control under some circumstances.

For these reasons, it would be desirable to provide improved devices and methods for crossing vascular occlusions or other blockages formed within blood vessels in order to treat the occlusion as well as to create pathways for the placement of guidewires, interventional devices and catheters. In particular, it would be desirable to provide low profile devices for creating centered passages through an occlusion with a high degree of control and a reduced resistance to advancement of the device. Such devices should be relatively inexpensive to produce and relatively simple to use. At least some of these objectives will be met by the inventions described herein below.

2. Description of the Background Art. U.S. Pat. No. 9,060,806 has been described above. The following patents and publications are also of interest: U.S. Pat. Nos. 6,599, 304; 7,763,012; 8,021,330; 8,062,316; 8,241,315; 8,361, 094; 8,556,926; US2002/0128677; US2005/0038462; US2005/0171572; US2005/0216044; US2006/0074442; US2007/0083193; US2008/0281323; US2009/0270714; US2010/0082051; US2010/0168557; US2011/0022045; US2012/0253186; US2012/0283565; and US2014/0277009.

SUMMARY OF THE INVENTION

In a first aspect, the present invention provides a catheter for centrally crossing an occluded blood vessel. The catheter comprises a tubular catheter body having a distal end, a proximal end, and a central passage therethrough. A rotatable drive shaft extends through the central passage of the tubular catheter body and has a distal end, a proximal end, and a central lumen therethrough. A cutting tip is mounted on the distal end of the rotatable drive shaft, and the cutting tip is configured to cut through occlusive material, such as plaque, calcified plaque, clot, thrombus, and the like, when rotated. The cutting tip has a passage contiguous with the central lumen of the rotatable drive shaft. As described in detail below, the contiguous passage and lumen allow guidewire placement after the occlusion has been crossed and a centered passage through the occlusion has been created.

The crossing catheters of the present invention have a particular centering mechanism which accurately centers a distal region of the catheter as the cutting tip is rotated to create a passage through the vascular occlusion. The centering mechanism is particular beneficial as it has a low "crossing" profile (circumferential width) that allows it to be pushed through the occlusive material but presents a large circumferential surface area for engaging the vascular wall to minimize the trauma. More specifically, the centering mechanism comprises a plurality of flat springs, usually flat spiral springs as described in more detail below, disposed circumferentially about a distal region of the tubular catheter body. The flat springs are adapted to elastically self-expand from a radially constrained configuration to a radially expanded configuration so that they can be deployed after the catheter has been advanced to a location near the occlusion in a target blood vessel. Each flat spring has a (1) wide lateral surface configured to atraumatically engage a wall region of the blood vessel to centrally align the tubular catheter body in a lumen in the blood vessel and (2) a narrow distal edge configured to penetrate the occlusion as the catheter is distally advanced. In specific examples, the flat springs are cut from a tubular element so that the flat springs are initially portions of a cylinder and deploy by radially unfolding from the cylinder to extend radially outwardly in a spiral pattern to engage the blood vessel wall.

In preferred embodiments of the present invention, the cutting tip will be rotated by a manual mechanism allowing the treating physician to advance the catheter inclusion while manually controlling the cutting action of the tip. In particular, the physician will be able to observe progress of the cutting tip fluoroscopically, and when combined with tactile feedback, the physician can manually control the rate of advancement and the rate of rotation of the cutting tip to optimally advance the catheter to create the desired center passage through the occlusion. Conveniently, the cutting tip may be manually driven by a wheel or spindle disposed in a handle at the proximal end of the catheter.

The dimensions of the catheter will generally be from 120 cm to 150 cm in length from 5 Fr to 7 Fr (one French (Fr) equals 0.33 mm) in diameter, with specific dimensions depending on the catheter's intended use. For example, catheters intended for treating the coronary arteries will typically have a length in the range from 130 cm to 150 cm and a diameter from about 5 Fr to 7 Fr For peripheral devices, the tubular catheter body will typically have a length in the range from 120 cm to 140 cm and a diameter in the range from 5 Fr to 7 Fr.

The cutting tip may take a variety of configurations. Particularly preferred is a cutting tip which includes at least one cutting loop, often two cutting loops, extending in the distal direction from a distal end of the cutting tip. For coronary applications, a single cutting loop may be radially offset from a guidewire port axially aligned with the passage through the cutting tip or two cutting loops may be disposed symmetrically on opposite sides of the guidewire port. For peripheral applications, the cutting loop may be centered on the cutting tip and the passage through the cutting tip will be inclined or radially offset from the central axis of the cutting tip to direct a guide wire away from the cutting loop or a pair of cutting loops may be symmetrically positioned on the cutting tip as with the coronary designs.

In other aspects of the present invention, each of the plurality of spiral or other flat springs may have a Ω-shape with a base portion attached to the tubular catheter body and a loop portion extending radially away from the tubular catheter body. In other cases, the plurality of spiral flat springs will consist of three spiral flat springs. In such cases, the three spiral flat springs will usually be spaced circumferentially apart by 120°. Conveniently, the spiral flat springs may be fabricated by laser cutting or otherwise patterning a tubular blank formed from an elastic material, usually an elastic metal, more usually a superelastic metal, such as a nickel-titanium alloy (e.g. Nitinol® alloy).

In a second aspect of the present invention, a method for centrally crossing an occluded blood vessel comprises advancing a catheter through an occlusion in the blood vessel. A cutting tip is rotated or rotationally oscillated on a distal end of the catheter to cut or abrade a path through the occlusive material as the catheter is advanced. In order to center the catheter during the cutting procedure, a plurality of spiral or other flat springs are deployed or unfurled from a distal portion of the tubular catheter body. A wide lateral surface on each of the flat springs atraumatically engages a wall region of the blood vessel to centrally align a distal region of the catheter body in a lumen of the blood vessel while a narrow distal edge of each of the flat springs penetrates through the occlusion as the catheter is advanced, typically compressing and/or cutting the plaque or thrombus to enlarge the passage initially formed by the cutting tip.

In specific embodiments of the method, the cutting tip is manually oscillated or rotated, typically by rotating a cylinder or wheel on a handle attached to a proximal end of the catheter. Unfurling the plurality of spiral flat springs typically comprises releasing the spiral flat springs from radial constraint so that they can elastically self-expand, typically by advancing a distal portion of the catheter from a sheath or guiding catheter which constrains the spiral flat springs as the catheter prior to advancing the cutting tip through the occlusion.

In further specific embodiments, the centering catheter may be used to place a guidewire through the passage created by the catheter. For example, the catheter may carry and optionally utilize a guidewire for initial placement. That guidewire can also be used to assist in advancing the catheter across an occlusion. After the catheter has crossed the occlusion, the guidewire may be left in place through the occlusion for advancement of further interventional and/or diagnostic devices. In other instances, however, the centering catheter can be advanced to, but not through, an occlusion, and used as a platform for advancing guidewires and other devices into the occlusion, The centering catheter can provide an excellent platform for advancing tools into and/or through the center of an occlusion. In still other cases, a second guidewire may be exchanged for an initial placement guidewire when a guidewire with different characteristics is needed.

In some instances, while the catheter remains centered, a guidewire or other tool can be advanced and penetrated through a distal face of the occlusion. After penetration of the distal face, the cutting catheter can then be advanced. In still other embodiments, the catheter can be advanced using the cutting tip until a proximal face of the occlusion is approached. Before cutting through the proximal face of the occlusion, however, guidewire can be deployed from the centering catheter and passed through the distal face of the occlusion. The cutting and centering catheters of the present invention are thus useful for a wide variety of specific protocols requiring or benefitting from a central alignment of the catheter with the occlusion.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
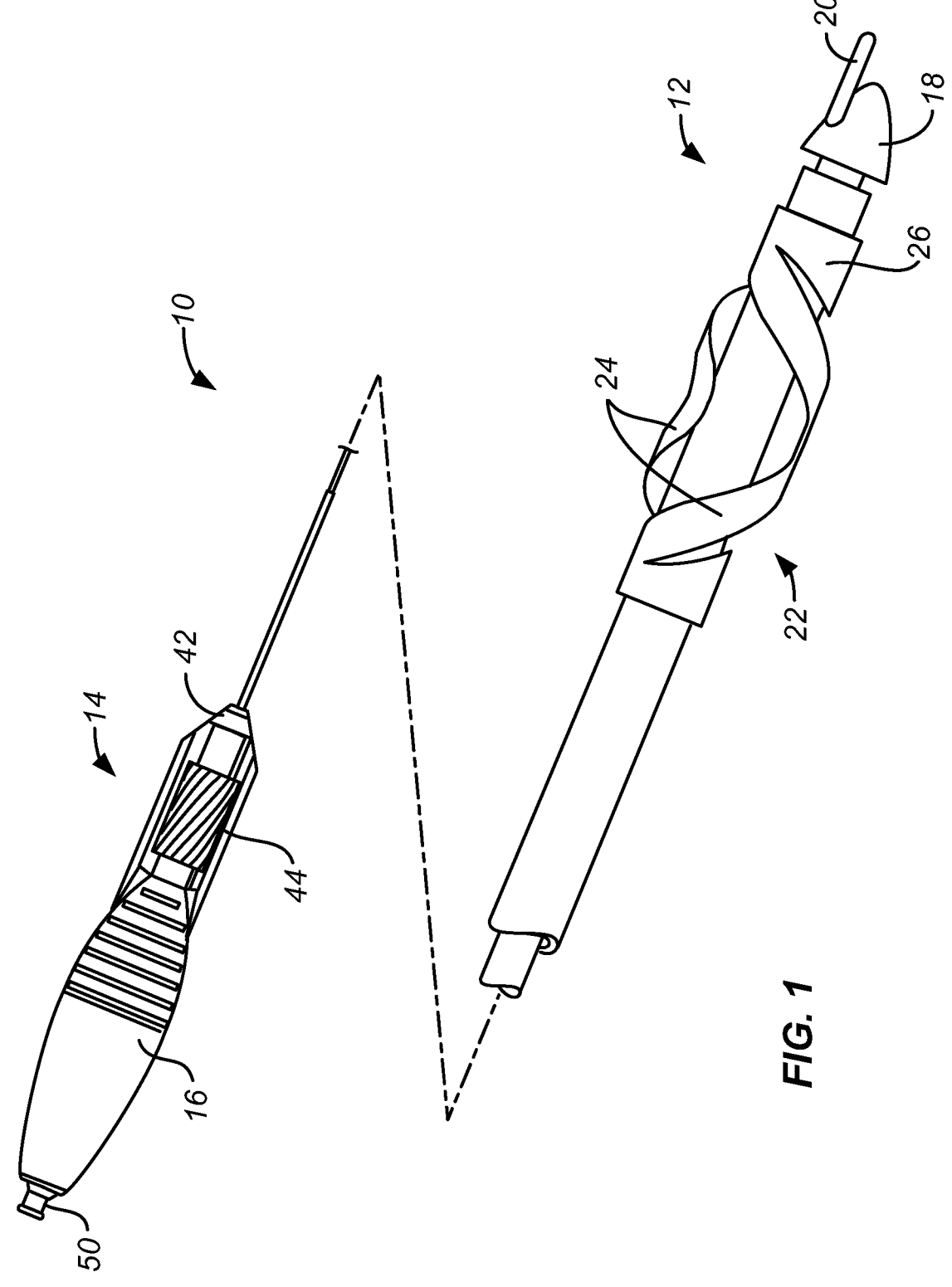
FIG. 1 illustrates a first embodiment of a catheter for centering and crossing a vascular occlusion constructed in accordance with the principles of the present invention.

Referring now to FIG. 1, a catheter 10 for centering and crossing vascular occlusions comprises a catheter body having a distal end portion 12 and a proximal end 14 having a proximal handle 16 thereon. A rotatable cutting tip 18 is located at a distal tip of the distal end portion 12 and includes a single cutting loop 20 which may be rotated as described in more detail below. A centering cage 22 circumscribes the distal end portion 12 to maintain centering of the distal end portion 12 within a vascular lumen as the catheter 10 is advanced therethrough. In particular, the centering cage 22 includes a plurality (three as illustrated) of planar, usually spiral springs 24. The spiral springs are preferably formed by cutting or otherwise patterning a cylindrical tube 26, where the entire tube may then be secured to the distal end portion 12 of the catheter 10. The cylindrical tube 26 will typically be formed from nitinol or other elastic metal and will be heat set so that the individual spiral springs 24 are in their radially expanded configuration in the absence of a radial constraint, such as a delivery sheath, guide catheter, or the like.

Figure 2:
FIG. 2 is a longitudinal cross-sectional view of a distal portion of the catheter for centering and crossing a vascular occlusion of FIG. 1 shown with a centering cage in a radially expanded configuration.
Figures 3A, 3B:
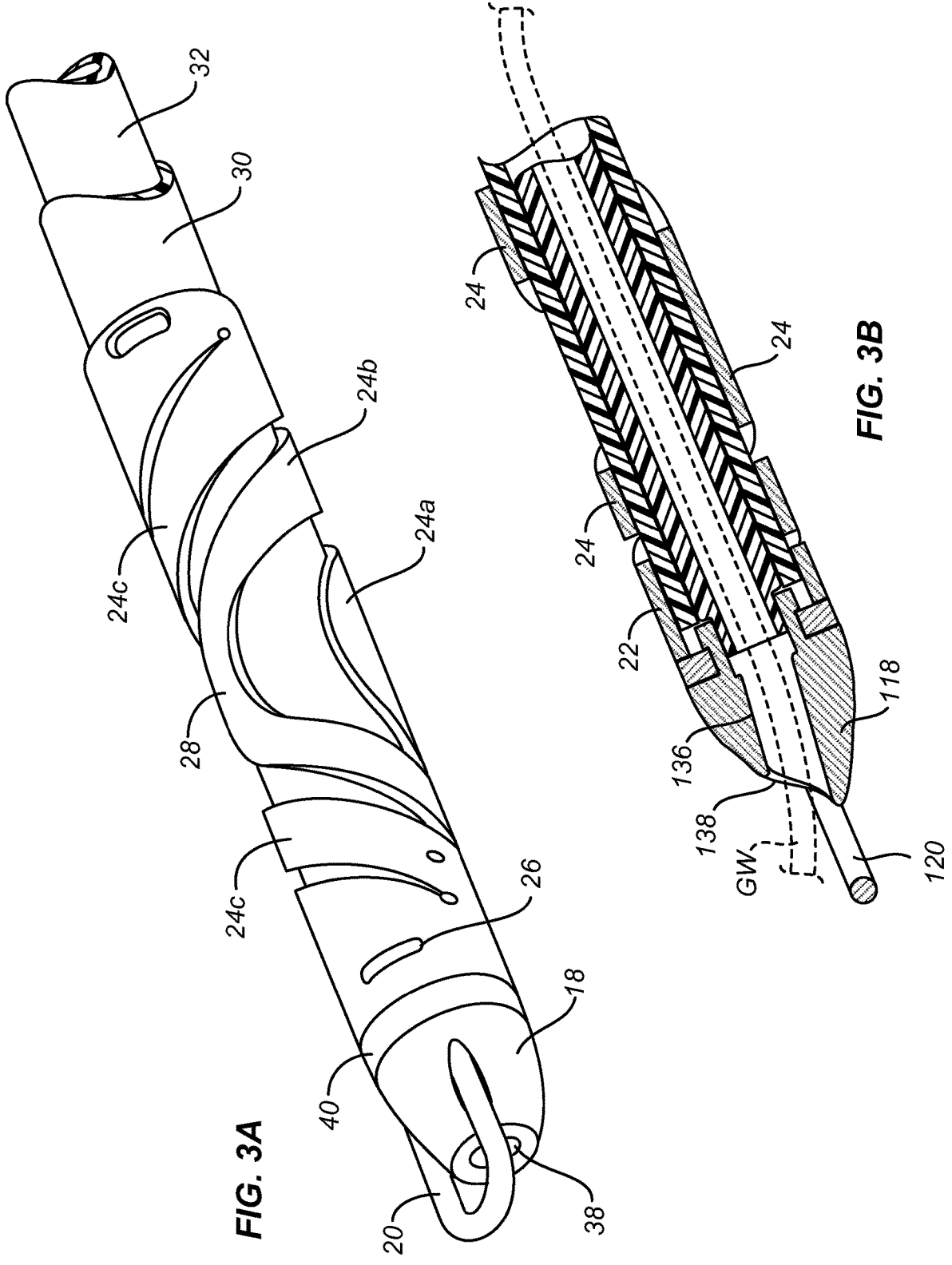
FIG. 3A is an alternative view of the distal portion of the catheter for centering and crossing a vascular occlusion of FIG. 1 shown with the centering cage in a radially constrained configuration.
FIG. 3B illustrates a distal portion of an alternative embodiment of a catheter for centering and crossing a vascular occlusion constructed in accordance with the principles of the present invention of a type particularly intended for treating occlusions in the peripheral; vasculature.

Referring now also to FIGS. 2 and 3A, the catheter 10 includes an outer shaft 30 and an inner drive shaft 32. The inner drive shaft 32 is concentrically disposed within a luminal passage of the outer shaft and is rotatable therein as will be described in more detail below. The inner drive shaft 32 also has a lumen 34 which is configured to accommodate a guidewire GW as well as for other purposes, such as infusion, suction, and the advancement of other interventional tools.

The cutting tip 18 has a central passage 36 which is aligned and contiguous with the lumen 34 of the inner drive shaft. The central passage 36 has a distal opening 38 through which a guidewire or other element, tool, or component may be advanced. The cutting tip 18 is fixedly attached to a distal end of the inner drive shaft 32 so that rotation of the inner drive shaft will cause rotation of the cutting tip 18 as well as the cutting loop 20. A retaining ring 40 is provided to hold the inner drive shaft 32 within the central luminal passage of the outer shaft 30.

While the central passage 36 of the cutting tip 18 will typically be axially aligned with the lumen 34 of the inner drive shaft, in other embodiments, such as those intended for peripheral use as shown in FIG. 3B, a cutting tip 118 will have a centrally aligned cutting loop 120 which has a passage 136 which is inclined or offset relative to its longitudinal axis so that the distal opening 138 deflects the guidewire away from the cutting loop 120. All other components and numbering shown in FIG. 3B are identical to those in the previous figures.

Figure 4:
FIG. 4 illustrates an alternative cutting tip with two cutting loops and a fluted distal cutting surface.

Referring now to FIG. 4, a catheter 100 according to the present invention may have an alternative cutting tip 118 design with a pair of cutting loops 20a and 20b disposed on either side of a distal guidewire port 112, typically being placed symmetrically about the port. In addition a plurality of flutes 154 may be formed in a distal surface of the cutting tip 118 to further aid in cutting through plaque or clot as the tip is rotated or rotationally oscillated at the catheter is advanced. A centering cage 122 may be formed with a plurality of spiral or other flat springs 124 having flat surfaces 128 when deployed radially outwardly to engage the vessel wall as the catheter is advanced. While centering cage 12 is similar to cage 22 described previously, cage 124 may have a shorter length to facilitate advancement through tortuous regions of the vasculature, particularly the coronary vasculature. An outer shaft 130 and an inner drive shaft 132 may have constructions similar or identical to the constructions described previously for outer shaft 30 and inner drive shaft 32.

Figure 5:
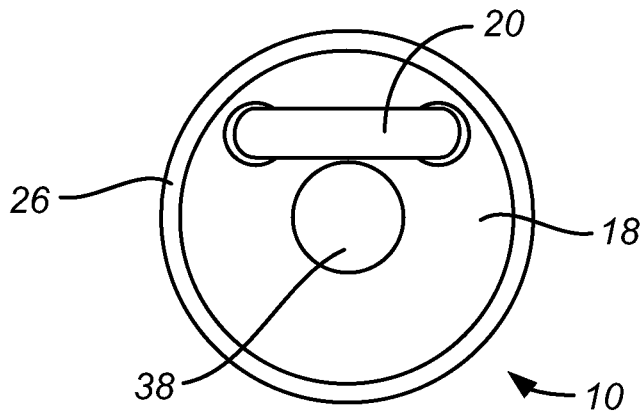
FIG. 5 is a front view of distal portion of the catheter for centering and crossing a vascular occlusion of FIG. 1 shown with a centering cage in a radially constrained configuration.
Figure 6:
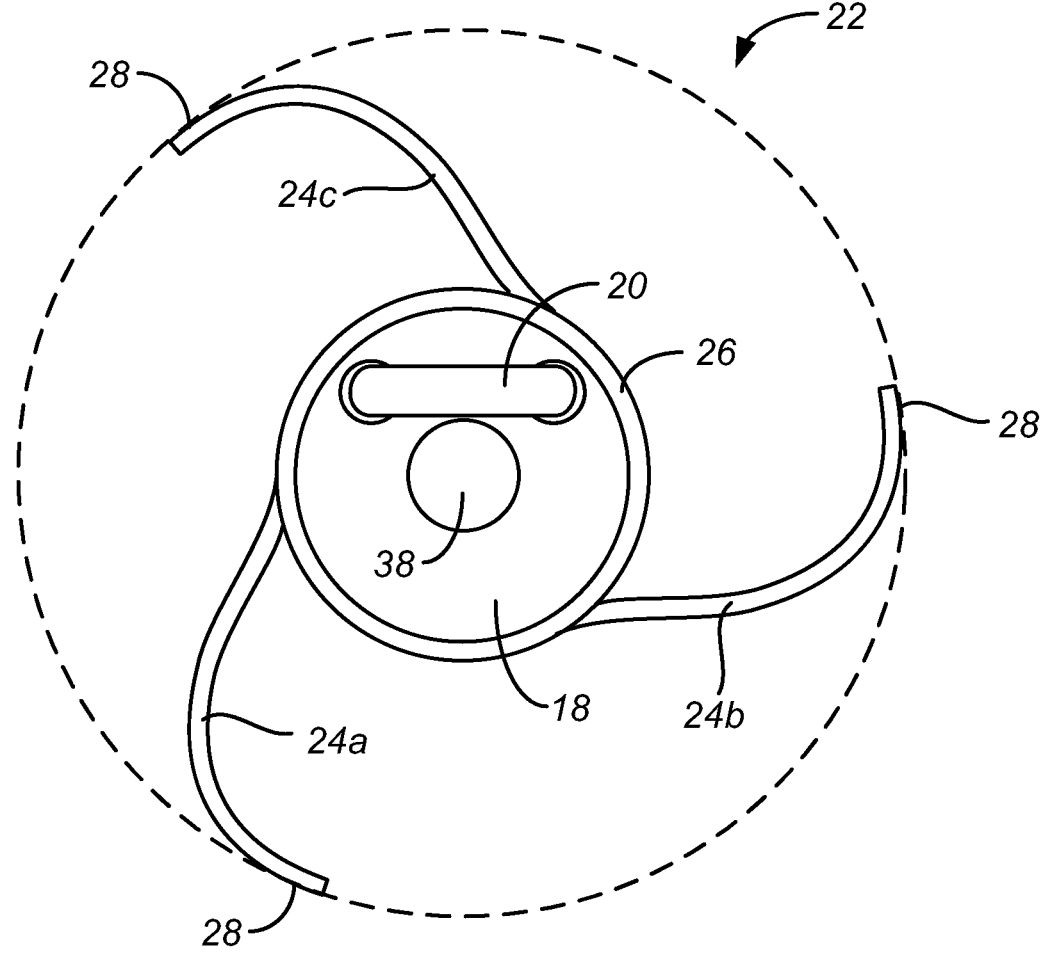
FIG. 6 is a front view of distal portion of the catheter for centering and crossing a vascular occlusion of FIG. 1 shown with a centering cage in a radially expanded configuration.

Referring now to FIGS. 5 and 6, when radially constrained, the spiral centering springs 24 will generally be collapsed within an envelope defined by the cylindrical tube 26, as shown in FIG. 5. When released from constraint, in contrast, each of the three spiral centering springs 24a, 24b and 24c will radially open to define flat surfaces 28 having an effective diameter shown in broken line. The particular contours and flat surfaces defined by each of the spiral centering springs can be determined by thermal setting of the nitinol or other shape memory metal during fabrication of the centering cage 22. As also observed in FIG. 6, the leading edge of each of the spiral centering springs 24 has a very low profile which allows the centering springs to be advanced through occlusive material with a reduced resistance to pushing.

Figures 7, 8:
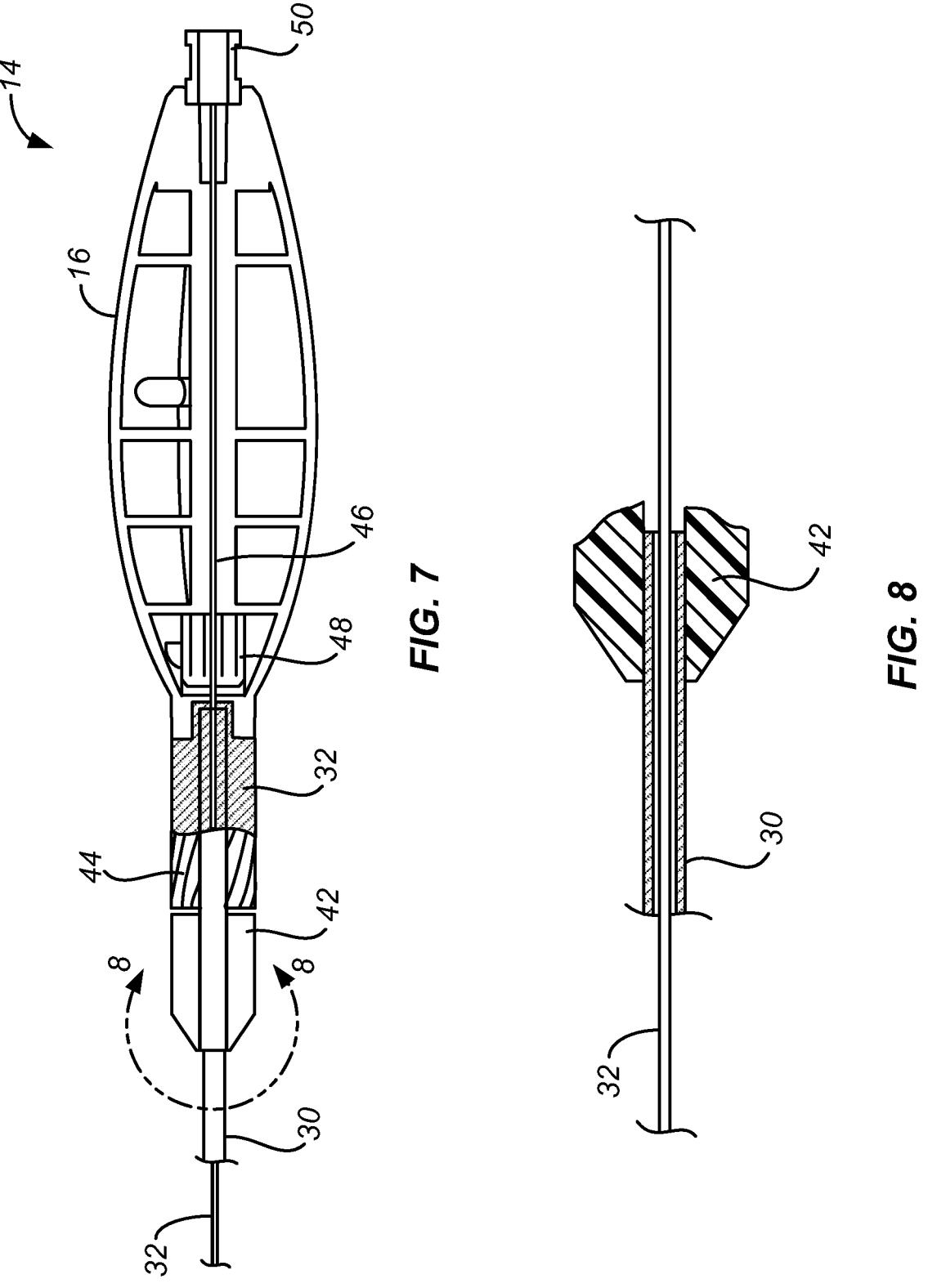
FIG. 7 is a partial cross-sectional view of a proximal handle of the catheter for centering and crossing a vascular occlusion of FIG. 1.
FIG. 8 is a detailed cross-sectional view of a distal end of the proximal handle of FIG. 7 taken along line 8-8 of FIG. 7.

The handle 16 is best illustrated in FIGS. 7 and 8. The handle 16 has a nose 42 which is attached to the proximal end of the outer shaft 30 of the catheter body. The outer shaft is fixedly attached so that the outer will be prevented from rotating relative to the handle. In contrast, the inner drive shaft 32 is attached to a wheel or spindle 44 which is rotatably mounted in the handle 16 to permit manual rotation of the wheel or spindle relative to the handle. Rotation of the wheel or spindle 44, in turn, will rotate the inner drive shaft 32 which and in turn rotates the distal cutter 18 and cutting loop 20. A proximal end of the inner drive shaft 32 (located proximately of the wheel or spindle 44) passes through a bearing connector 48 and is received within a transition tube 46 which leads to a luer fitting 50 at a proximal end of the handle. The luer and transition tube will be rotationally fixed within the handle, and the proximal end of the inner drive shaft 32 and distal end of the transition tube 46 will form a rotating seal in the bearing connector. It will be appreciated that guidewires and other interventional elements may be introduced through the luer 50 and lumen of the inner drive shaft 32 so that they may be advanced to the distal tip of the catheter and out through the distal opening 38 of the cutting tip 18.

Figure 9A:
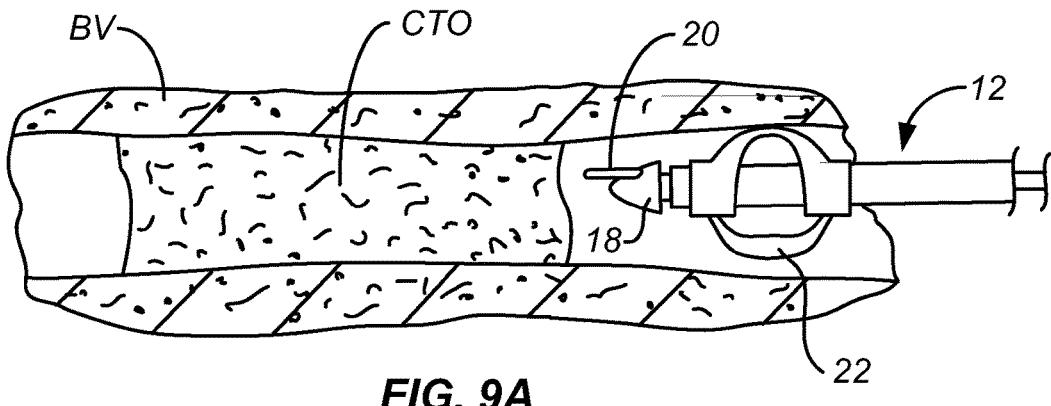
FIGS. 9A-9C illustrate the use of the catheter of FIG. 1 for centering and crossing a vascular occlusion and thereafter advancing a guidewire through the path created.
Figure 9B:
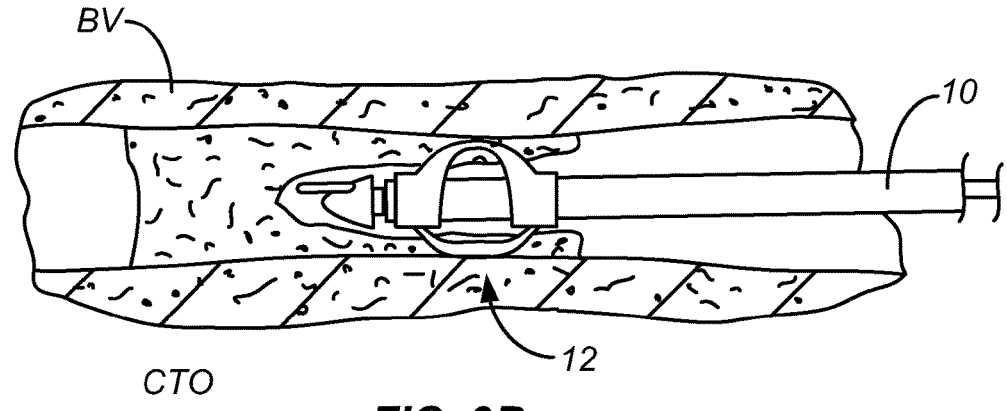
Figure 9C:
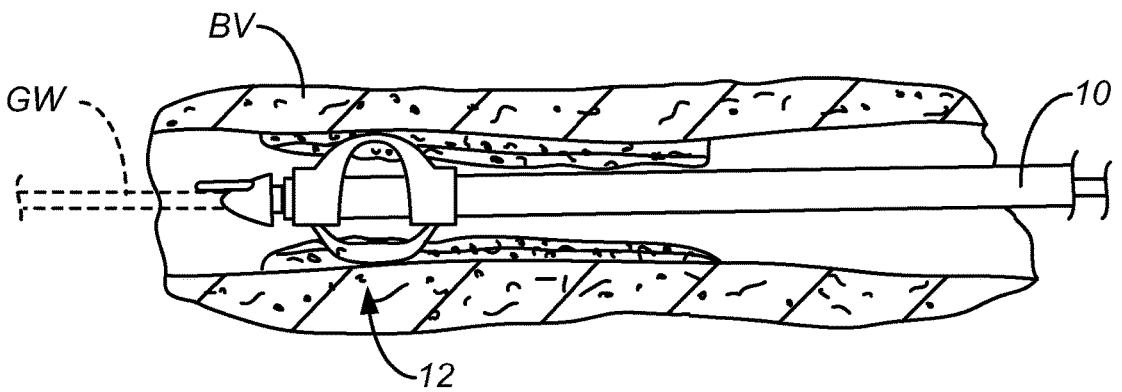

Referring now to FIGS. 9A through 9D, the catheter 10 for centering and crossing occlusions may be advanced through a chronic total occlusion CTO in a blood vessel BV, as illustrated. The distal end portion 12 of the catheter 10 is initially advanced so that the cutting loop 20 lies immediately proximal to a proximal surface of the chronic total occlusion CTO. The user then manually rotates the cutting tip 18 and cutting loop 20 while advancing the catheter to penetrate through the proximal face of the occlusion and begin to create a central passage therethrough. The spiral centering springs 24 of the centering cage 22 engage the inner walls of the blood vessel and maintain centering of the distal region 12 of the catheter as the catheter is advanced. As described previously, the flat surfaces of the springs atraumatically engage the vessel wall while the low width of each spring allows the centering cage to pass through the occlusive material with reduced resistance. The catheter can be incrementally advanced as the user manually rotates the cutting tip and observes the progress fluoroscopically. The procedure may be complete when the distal tip of the catheter passes through a distal face of the occlusion, as shown in FIG. 9C. After the catheter has reached the position shown in FIG. 9C, a guidewire GW may be placed, catheter 10 is removed and/or other interventional procedures may be performed.

Figure 10:
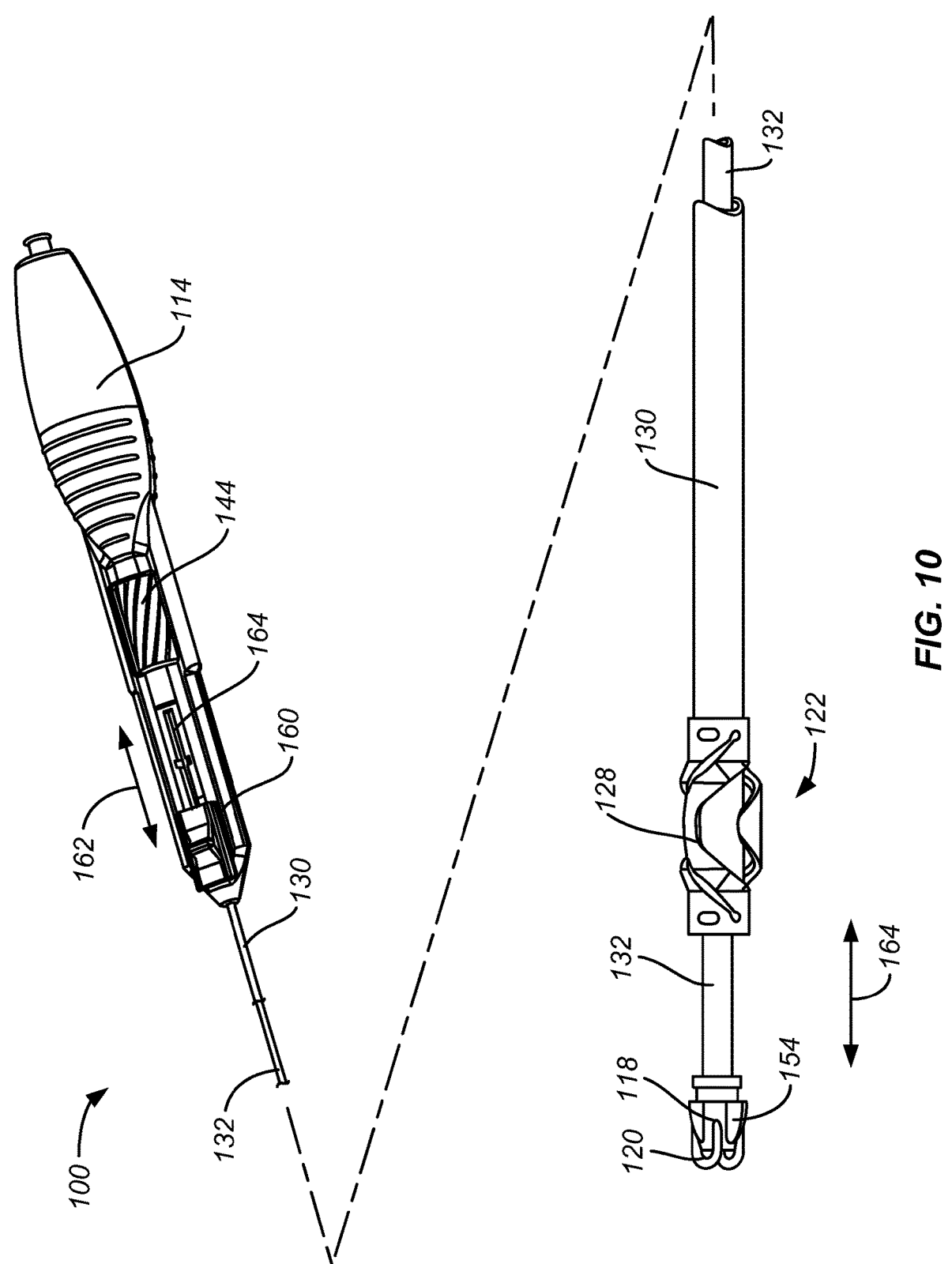
FIG. 10 illustrates an alternative embodiment of the centering and crossing catheter of the present invention having a cutting tip that may be distally advanced relative to a centering cage to facilitate advancement of the catheter through tortuous vasculature.

Referring now to FIG. 10, catheter 100 having the cutting tip 118 illustrated in FIG. 4 may be further modified to allow axial advancement and retraction of the cutting tip relative to the centering cage 122. In particular, a thumb slide 160 may be positioned in a slot 164 in a wall of handle 114, preferably located distal to the wheel 144. The thumb slide is coupled to the outer member 130 so that by sliding the thumb slide axially, as indicated by arrow 162, the outer member and its distally attached centering cage 122 may be axially advanced and retracted, typically over a range from 3 cm to 4 cm, relative to the inner member 132 and cutting tip 118, as indicated by arrow 164. The ability to de-couple a distal segment of inner member shaft and the attached cutting tip 118 is a significant advantage when advancing the catheter through tortuous vasculature, such as coronary vasculature, where the cutting tip and distal inner member shaft may be first advanced past a tight and/or narrow curve in the vasculature with the centering cage 122 being separately advanced thereafter coaxially over the inner member shaft.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for centrally crossing an occluded blood vessel, the method comprising:

advancing a catheter through an occlusion in the blood vessel; and rotating or rotationally oscillating a cutting tip mounted on a distal end of the catheter to cut through occlusive material as the catheter is advanced, creating a passage through the occlusion;

wherein a plurality of flat springs elastically self-expand from a radially constrained configuration to a radially expanded configuration to (1) atraumatically engage a wide lateral surface of each flat spring against a wall region of the blood vessel to centrally align at least the cutting tip of said catheter in a lumen of the blood vessel as the catheter is advanced, and (2) penetrate a narrow distal edge on the each flat spring through the occlusion as the catheter is advanced;

wherein the plurality of flat springs are proximal of and distinct from the cutting tip.

2. The method for centrally crossing an occluded blood vessel as in claim 1, wherein rotating or rotationally oscillating the cutting tip comprises manually rotating or rotationally oscillating the tip.

3. The method for centrally crossing an occluded blood vessel as in claim 2, wherein manually rotating or rotationally oscillating the tip comprises rotating or rotationally oscillating a cylinder on a handle attached to a proximal end of the catheter.

4. The method for centrally crossing an occluded blood vessel as in claim 1, wherein the flat springs comprise spiral flat springs.

5. The method for centrally crossing an occluded blood vessel as in claim 4, wherein the distal edge of the spiral flat springs is sharp.

6. The method for centrally crossing an occluded blood vessel as in claim 4, wherein the spiral flat springs selfdeploy from a distal portion of the catheter after releasing the spiral flat springs from radial constraint so that they elastically self-expand.

7. The method for centrally crossing an occluded blood vessel as in claim 6, wherein releasing the flat springs from radial constraint comprises advancing the distal end of the catheter beyond a distal end of a guide catheter.

8. The method for centrally crossing an occluded blood vessel as in claim 1, further comprising withdrawing the catheter and the cutting tip over a guidewire disposed in a central passage of the catheter and the cutting tip to leave the guidewire in the blood vessel lumen.

9. The method for centrally crossing an occluded blood vessel as in claim 8, wherein the catheter and the cutting tip had been advanced fully through an occlusion prior to being retracted to leave the guidewire in place fully through the occlusion.

10. The method for centrally crossing an occluded blood vessel as in claim 1, wherein the distal edge of the flat springs is sharp.

11. The method for centrally crossing an occluded blood vessel as in claim 1, wherein rotating or rotationally oscillating the cutting tip mounted on the distal tip of the catheter to cut through occlusive material as the catheter is advanced enlarges the passage in the occluded blood vessel.

12. The method for centrally crossing an occluded blood vessel as in claim 1, wherein the distal edge on the each flat spring penetrates through the occlusion, compresses the occlusive material radially outward, or both to enlarge the passage as the catheter is advanced.

13. The method for centrally crossing an occluded blood vessel as in claim 1, further comprising enlarging the passage by rotating or rotationally oscillating the cutting tip mounted on the distal tip of the catheter to cut through occlusive material as the catheter is advanced, wherein distal edge on the each flat spring further penetrates through the occlusion, compresses the occlusive material radially outward, or both to enlarge the passage as the catheter is advanced.

14. The method for centrally crossing an occluded blood vessel as in claim 1, wherein the plurality of flat springs are deployed laterally outwardly from a tubular body of the catheter.

15. The method for centrally crossing an occluded blood vessel as in claim 1, wherein the plurality of flat springs consists of three flat springs.

16. The method for centrally crossing an occluded blood vessel as in claim 15, wherein the three spiral flat springs are spaced circumferentially apart by 120°.

17. The method for centrally crossing an occluded blood vessel as in claim 1, wherein the plurality of flat springs are disposed circumferentially around a distal region of the catheter.

18. The method for centrally crossing an occluded blood vessel as in claim 1, wherein the plurality of flat springs have a low circumferential width and a large circumferential surface area for engaging with the wall region of the blood vessel.

19. The method for centrally crossing an occluded blood vessel as in claim 1, wherein the plurality of flat springs are distributed substantially evenly around a circumference of the catheter.

\* \* \* \* \*